(12) United States Patent
Yao et al.

(10) Patent No.: US 7,988,632 B2
(45) Date of Patent: Aug. 2, 2011

(54) METHOD AND APPARATUS FOR FAST 3D ULTRASOUND IMAGING

(75) Inventors: Bin Yao, Shenzhen (CN); Yong Tian, Shenzhen (CN); Qinjun Hu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 913 days.

(21) Appl. No.: 11/875,773

(22) Filed: Oct. 19, 2007

(65) Prior Publication Data

US 2008/0262355 A1    Oct. 23, 2008

(30) Foreign Application Priority Data

Apr. 23, 2007   (CN) .......................... 2007 1 0103118

(51) Int. Cl.
*A61B 8/00*   (2006.01)
(52) U.S. Cl. ........................................ 600/443; 600/437
(58) Field of Classification Search ........................... None
See application file for complete search history.

(56) References Cited

U.S. PATENT DOCUMENTS

| | | | |
|---|---|---|---|
| 5,840,034 A | | 11/1998 | Amemiya et al. |
| 5,911,691 A | * | 6/1999 | Mochizuki et al. ........... 600/443 |
| 6,102,861 A | | 8/2000 | Avila et al. |
| 6,102,864 A | | 8/2000 | Hatfield et al. |
| 6,155,978 A | * | 12/2000 | Cline et al. ..................... 600/443 |
| 2005/0187474 A1 | * | 8/2005 | Kwon ........................... 600/437 |

FOREIGN PATENT DOCUMENTS

| | | |
|---|---|---|
| CN | 1354834 | 6/2002 |
| CN | 1518668 | 8/2004 |
| CN | 1529158 | 9/2004 |
| CN | 1636521 | 7/2005 |
| CN | 1742682 | 3/2006 |
| CN | 1973776 A | 6/2007 |
| JP | 2005031061 | 2/2005 |

* cited by examiner

*Primary Examiner* — Unsu Jung
*Assistant Examiner* — Nigel Fontenot
(74) *Attorney, Agent, or Firm* — Kory D. Christensen; Stoel Rives LLP (57) ABSTRACT

The present invention provides a method and apparatus for fast 3D ultrasound imaging. The method comprises data acquisition, desired data selection, data smoothing, table construction, ray casting, table look-up, ray synthesis and final result output. The apparatus comprises an acquisition module, a table look-up module, a synthesis module and an output module. The present invention can avoid a huge amount of unnecessary reconstruction calculations by smoothing preprocessing and constructing the reconstruction table and the gradient table as well as transforming coordinates of the points where necessary. The present invention has greater practical applicability, because the existing imaging technology demands that the radius for rotating the probe be identical to the radius of the probe.

20 Claims, 9 Drawing Sheets

(prior art)

Fig.1

(prior art)

Fig.2

(prior art)

METHOD AND APPARATUS FOR FAST 3D ULTRASOUND IMAGING

STATEMENT OF RELATED APPLICATION

The present application claims priority of the Chinese Patent Application No. 200710103118.7, entitled "A Method and Apparatus for Fast 3D Ultrasound Imaging", filed on Apr. 23, 2007, which is incorporated herein by reference in its entirety.

FIELD OF THE INVENTION

The present invention relates to an imaging method and apparatus, and more particularly to a method and apparatus for 3D ultrasound imaging.

BACKGROUND OF THE INVENTION

Currently, the most general application of 3D ultrasound imaging is to image a fetus in an obstetrical department, so that it can be observed clearly in clinic whether the fetus in a pregnant women's belly suffers from harelip, umbilical cord around neck etc. Additionally, the 3D ultrasound imaging can be used to observe gallbladder, bladder etc. The characteristics of such existing 3D imaging are that the imaged tissue motions rather slowly and the requirements as to time resolution are not high. In this case, the tissue to be imaged can be scanned using a common 1D probe driven by a free arm or a mechanical probe driven by a motor. The mechanical probe works generally at a speed of 2-4 frames per second. An advanced 3D ultrasound imaging, which targets at the organs which motion at higher speed such as heart, is mainly a 3D high-speed imaging using a 2D probe. Since the 2D probe is capable of obtaining data at a rather high speed, a relatively high time resolution can be reached, generally at 20 frames per second.

The 3D imaging process mainly includes data acquisition, data processing and imaging.

Data acquisition is a process of collecting volume data desired for 3D imaging. Taking a 1D probe driven by a free arm as an example, desired volume data are image sequences scanned by moving the 1D probe uniformly along the elevation direction of the probe. The volume data includes 3D information about the portion scanned by the probe, which is useful for 3D imaging. A mechanical probe is driven around a fulcrum by a motor, so that the desired volume data can be obtained in sector scanning way. A series of scanning line data are to be obtained in the data acquisition stage, which can also be considered as a series of image sequences before coordinate transformation. Each point in these data corresponds to a scanned point constituting the 3D object, which is referred to as a voxel.

Data processing is a process in which the acquired data is processed prior to imaging. It generally comprises data reconstruction, in which the collected polar coordinates are transformed into Cartesian coordinate. By said coordinate transformation, it is possible to obtain volume data in compliance with the real object, and the relative positions of the voxels are consistent with the real configuration.

Having been so processed, the volume data are then utilized for imaging. One of the most common imaging methods is the ray tracing method. Specifically, a viewpoint, a view plane and volume data are introduced into a virtual 3D space, and the volume data are re-sampled considering the line connecting the viewpoint to a pixel on the view plane as a ray direction. Finally, the re-sampled data are incorporated by a ray mathematical model to obtain a result that is the gray-scale value of the corresponding pixel on the view plane. When the gray-scale values for all pixels have been obtained, the imaging is finished.

The U.S. Pat. No. 5,911,691, assigned to Aloka, entitled "Ultrasound image processing apparatus and method of forming and displaying ultrasound images by the apparatus" describes a ray tracing method for 3D imaging in details.

Figure 1:
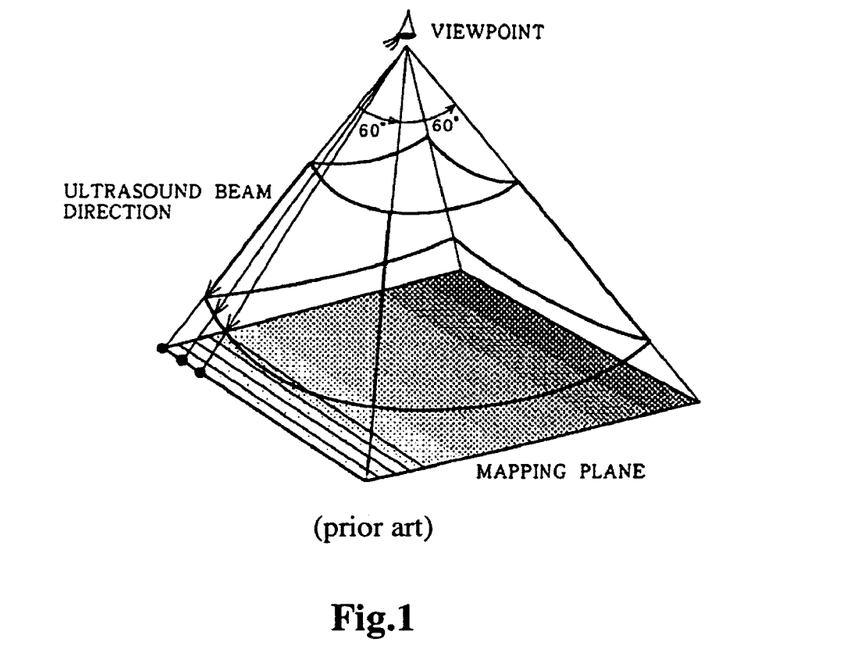
FIG. 1-3 are schematic diagrams illustrating an existing method for acquiring volume data and an existing ray tracing method.

As shown in FIG. 1, the above-mentioned patent suggests collecting data according to the position of a viewpoint. For a 1D mechanical probe, the radius for rotating the probe is identical to the radius of the probe, so that the obtained scanning line directions can extend to converge at the same point. Taking this point as the viewpoint, the ray direction coincides with the scanning line direction. That is to say, each of the scanning lines corresponds to a line that connects the viewpoint to a pixel on the view plane. Such a design significantly decreases the amount of calculation, because a) data reconstruction is no longer necessary; b) there is no need to calculate such parameters as an incident point etc. according to the ray direction or to perform a re-sampling operation.

Figure 2:
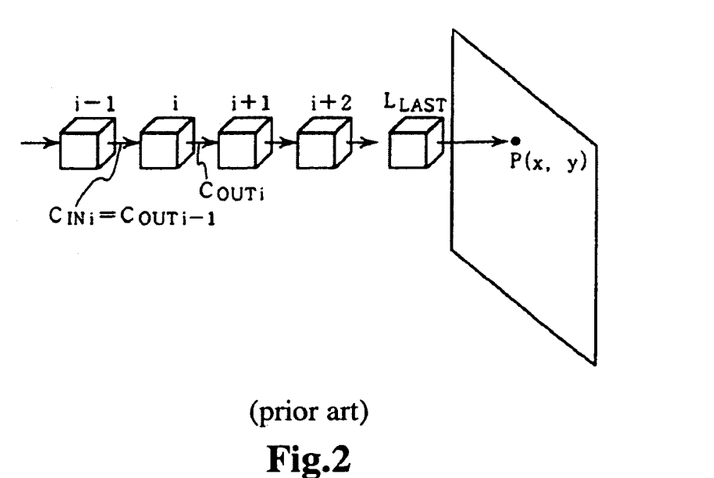
Figure 3:
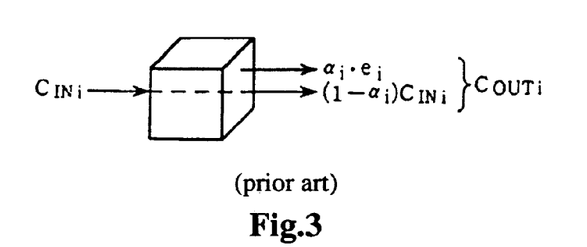

With respect to imaging, the above-mentioned patent employs a conventional ray tracing method. The only difference is that imaging is realized by merely calculating each scanning line. As shown in FIG. 2, each cube represents a voxel in a ray (i.e. the scanning line in the U.S. Pat. No. 5,911,691); the parallelogram represents the view plane, that is, the resultant image. All data concerning a certain ray are synthesized to obtain a pixel P (x, y). An iterative process is used in data synthesis, which is a simulated process in which the ray passes through different mediums (attributes of the medium are described by values of a corresponding data point) and is absorbed. Each voxel has an opacity to correspond to a different gray-scale value, which is generally presented as a monotonic curve proportional to the gray-scale value. The opacity is denoted by $a_i$ and the gray-scale of the voxel is denoted by $e_i$. Data synthesis is specified as follows:
  i) For the first voxel, $i=1$, $C_{INi}=0$;
  ii) $C_{OUTi}=(1-a_i)*C_{INi}+a_i*e_i$;
  iii) $i=i+1$, $C_{INi}=C_{OUTi-1}$;
  iv) if $$\sum_{k=1}^{i-1} a_i = 1$$

or i exceeds the range of the number of voxels, $C_{INi}$ is output; otherwise, skipping to ii).

The problem of the above-mentioned technical solution is that it relies on the probe in that the viewpoint, the rotary origin of the probe and the origin of the probe must coincide, which requires using a 2D probe or a particularly designed mechanical probe. This restricts the application of the technique. Moreover, once the viewpoint is fixed, such operations as magnifying and diminishing rotation cannot be carried out, because the operations will result in the ray deviating from the scanning line direction. Therefore, the above-described technical solution fails to decrease the amount of calculation, which is one of the important objects achieved by the present invention.

SUMMARY OF THE INVENTION

The object of the present invention is to overcome the shortcomings in existing method to provide a fast and accurate 3D ultrasound imaging method and apparatus using a conventional mechanical probe. In order to realize this goal, the following technical solutions are adopted in the present invention:

According to the first aspect of the embodiments of the present invention, there is provided a method for fast 3D ultrasound imaging, comprising the steps of: acquiring volume data in polar form by scanning with a mechanical ultrasound probe, and storing the volume data in a cache; constructing a reconstruction table and a gradient table, among which the reconstruction table contains relations for transforming a Cartesian coordinate system to a polar coordinate system, and the gradient table contains (p1,p2,p3) corresponding to a polar coordinate point (r, theta, phi), where $$G = (p1, p2, p3) = \left(\frac{\partial X}{\partial r}, \frac{\partial Y}{\partial theta}, \frac{\partial Z}{\partial phi}\right);$$

casting rays to determine an initial sampling point which is assigned with an initial gray scale and an initial opacity, and to obtain a Cartesian coordinate of the sampling point; looking up the reconstruction table to obtain a polar coordinate of the sampling point according to its Cartesian coordinate, which is then subjected to interpolation to derive the gray scale value of the sampling point; if the gray scale value meets a synthetic condition, calculating gradient of the sampling point through looking up the gradient table, and calculating inner product of unit vector of the gradient and unit vector of the ray direction as well as an accumulated gray scale and an accumulated opacity based on the inner product; and if the gray scale value does not meet the synthetic condition returning back to the previous ray casting step; and if a predetermined termination condition is satisfied, outputting the current accumulated gray scale as a result for the corresponding pixel on a resultant image, otherwise returning back to the previous ray casting step; for each pixel on the resultant image, the gray scale of ray synthesis is calculated by emitting rays to finally form the image.

Optionally, the method for fast 3D ultrasound imaging according to the first aspect of the embodiments of the present invention further comprises step of smoothing the acquired volume data.

According to the second aspect of the embodiments of the present invention, there is also provided a method for fast imaging of 3D ultrasound, comprising the steps of: acquiring volume data in polar form by scanning with a mechanical ultrasound probe, and storing the volume data in a cache; constructing a reconstruction table and a gradient table, among which the reconstruction table contains relations for transforming a Cartesian coordinate system to a polar coordinate system, and the gradient table contains (p1,p2,p3) corresponding to a polar coordinate point (r, theta, phi), where $$G = (p1, p2, p3) = \left(\frac{\partial X}{\partial r}, \frac{\partial Y}{\partial theta}, \frac{\partial Z}{\partial phi}\right);$$

casting rays to determine an initial sampling point which is assigned with an initial gray scale and an initial opacity, and to obtain a Cartesian coordinate of the sampling point; looking up the reconstruction table to obtain a polar coordinate of the sampling point according to its Cartesian coordinate, which is then subjected to interpolation to derive the gray scale value of the sampling point; if the gray scale value meets a synthetic condition, calculating gradient of the sampling point through looking up the gradient table, and calculating inner product of unit vector of the gradient and unit vector of the ray direction as well as an accumulated gray scale and an accumulated opacity based on the inner product; and if the gray scale value does not meet the synthetic condition returning back to the previous ray casting step; and if a predetermined termination condition is satisfied, outputting the current accumulated gray scale as a result for the corresponding pixel on a resultant image, otherwise returning back to the previous ray casting step; for each pixel on the resultant image, the gray scale of ray synthesis is calculated by emitting rays to finally form the image.

Optionally, the method for fast 3D ultrasound imaging according to the second aspect of the embodiments of the present invention further comprises step of smoothing the volume data at the sampling point and obtaining the smoothed data of the volume data at the position of the coordinates of the sampling point.

Optionally, the method for fast 3D ultrasound imaging according to the first or second aspect of the embodiments of the present invention also comprises step of designating a region of interest via an interface, selecting data concerning the region of interest from the cache and subjecting the selected data to the smoothing processing and the subsequent steps.

Preferably, the smoothing processing is a mean filter or a median filter, and carried out along the most uniform direction among various directions of the current point.

In the reconstruction table, the relations for transforming the Cartesian coordinate (x, y, z) to the polar coordinate (r, theta, phi) are as follows:

$$R'=\sqrt{y^2+z^2},$$

$$phi=\tan^{-1}(z/y);$$

$$r=|AP|-pr-\sqrt{(pr-fr+R')^2+x^2}-pr,$$

$$theta=\tan^{-1}(x/(pr-fr+R'));$$

in which the reconstruction table comprises a table for corresponding (y, z) with (R', phi) and a table for corresponding (x, R') with (r, theta). When rotation angle, inter-frame angle, scanning depth for B image or scanning angle are changed, the reconstruction table is reconstructed; otherwise, the reconstruction table is maintained for use. The looking up step specifically comprises: looking up the reconstruction table to obtain R' and phi through y and z coordinates and then looking up the reconstruction table to obtain r and theta through R' and x coordinates.

Calculating gradient of the sampling point by looking up the gradient table is to transform a Cartesian coordinate point P(x, y, z) into a polar coordinate point (r, theta, phi) and obtain (p1, p2, p3) by looking up the gradient table through (r, theta, phi) and then use (p1, p2, p3) as step lengths of three coordinate axes so as to calculate the gradient Grad as follows:

$$\begin{aligned}Grad &= (Gr, Gtheta, Gphi) \\ &= (V(r+\xi \cdot p1, theta, phi) - V(r-\xi \cdot p1, theta, phi), \\ &\quad V(r, theta+\xi \cdot p2, phi) - V(r, theta-\xi \cdot p2, phi), \\ &\quad V(r, theta, phi+\xi \cdot p3) - V(r, theta, phi-\xi \cdot p3))\end{aligned}$$

where the factor $\xi$ is used to control the step length, which can be selected to be 2.

The initial values assigned to the gray scale and the opacity are 0. The accumulated gray scale $I_{out}$ and the accumulated opacity $\alpha_{out}$ are calculated as follows respectively:

$$I_{out} = I_{in} + (1-\alpha_{in}) \cdot \alpha_i \cdot C_i \cdot T_i;$$

$$\alpha_{out} = \alpha_{in} + \alpha_i(1-\alpha_{in});$$

Where $I_{in}$ and $I_{out}$ are the accumulated gray scales; $\alpha_{in}$ and $\alpha_{out}$ are the accumulated opacities; $C_i$ and $\alpha_i$ are respectively the gray scale and the opacity of the pixel which the current ray traverses; and $T_i$ is the inner product of unit vector of the gradient and unit vector of the ray direction.

The synthetic condition is a threshold set for the gray scale of the current sampling point. If the gray scale is smaller than the threshold, the sampling point concerned is considered as noise and will not be involved in the synthesis. The threshold is 30 based on different noise levels of different machines.

The termination condition is set to meet one of the following conditions:

a) $\alpha_{out} < K$, where $K \leq 1$;

b) the volume data re-sampled with a ray progressing to the last point.

According to the third aspect of the embodiments of the present invention, there is provided an apparatus for fast 3D ultrasound imaging, comprising: an acquisition module for acquiring volume data in polar form by scanning, and storing the volume data in a cache; a construction module for constructing a reconstruction table and a gradient table, among which the reconstruction table contains relations for transforming a Cartesian coordinate system to a polar coordinate system, and the gradient table contains (p1,p2,p3) corresponding to a polar coordinate point (r, theta, phi), where $$G = (p1, p2, p3) = \left(\frac{\partial X}{\partial r}, \frac{\partial Y}{\partial theta}, \frac{\partial Z}{\partial phi}\right);$$

a ray casting module for casting rays to determine an initial sampling point which is assigned with an initial gray scale and an initial opacity, and to obtain a Cartesian coordinate of the sampling point; a table look-up module for looking up the reconstruction table to obtain a polar coordinate of the sampling point according to its Cartesian coordinate, which is then subjected to interpolation to derive the gray scale of the sampling point; a synthesis module for calculating gradient of the sampling point through looking up the gradient table if the gray scale value meets a synthetic condition, and calculating inner product of unit vector of the gradient and unit vector of the ray direction as well as an accumulated gray scale and an accumulated opacity based on the inner product; and returning back to the ray casting module if the gray scale value does not meet the synthetic condition; and an output module for outputting the current accumulated gray scale as a result for the corresponding pixel on a resultant image if a predetermined termination condition is satisfied; otherwise returning back to the ray casting module.

Optionally, the apparatus for fast 3D ultrasound imaging according to the third aspect of the embodiments of the present invention further comprises a smoothing module for smoothing the acquired volume data.

According to the fourth aspect of the embodiments of the present invention, there is also provided an module for fast 3D ultrasound imaging, comprising: an acquisition module for acquiring volume data in polar form by scanning, and storing the volume data in a cache; a construction module for constructing a reconstruction table and a gradient table, among which the reconstruction table contains relations for transforming a Cartesian coordinate system to a polar coordinate system, and the gradient table contains (p1,p2,p3) corresponding to a polar coordinate point (r, theta, phi), where $$G = (p1, p2, p3) = \left(\frac{\partial X}{\partial r}, \frac{\partial Y}{\partial theta}, \frac{\partial Z}{\partial phi}\right);$$

a ray casting module for casting rays to determine an initial sampling point which is assigned with an initial gray scale and an initial opacity, and to obtain a Cartesian coordinate of the sampling point; a table look-up module for looking up the reconstruction table to obtain a polar coordinate of the sampling point according to its Cartesian coordinate, which is then subjected to interpolation to derive the gray scale of the sampling point; a synthesis module for calculating gradient of the sampling point through looking up the gradient table if the gray scale value meets a synthetic condition, and calculating inner product of unit vector of the gradient and unit vector of the ray direction as well as an accumulated gray scale and an accumulated opacity based on the inner product; and returning back to the ray casting module if the gray scale value does not meet the synthetic condition; and an output module for outputting the current accumulated gray scale as a result for the corresponding pixel on a resultant image if a predetermined termination condition is satisfied; otherwise returning back to the ray casting module.

Optionally, the apparatus for fast 3D ultrasound imaging according to the fourth aspect of the embodiments of the present invention further comprises a smoothing module for smoothing the volume data at the sampling point to obtain the smoothed data of the volume data at the position of the coordinates of the sampling point.

Optionally, the apparatus for fast 3D ultrasound imaging according to the third or fourth aspect of the embodiments of the present invention further comprises a selection module for designating a region of interest via an interface, selecting data concerning the region of interest from the cache and transmitting the selected data to the smoothing module and the subsequent module for processing.

Preferably, the smoothing module performs a mean filter or a median filter on the volume data, in which smoothing is carried out along the most uniform direction among various directions of the current point.

In the reconstruction table, the relations for transforming the Cartesian coordinate (x, y, z) to the polar coordinate (r, theta, phi) are as follows:

$$R' = \sqrt{y^2 + z^2},$$

$$phi = \tan^{-1}(z/y).$$

$$r = /AP/-pr = \sqrt{(pr-fr+R')^2 + x^2} - pr,$$

$$theta = \tan^{-1}(x/(pr-fr+R'));$$

in which the reconstruction table comprises a table for corresponding (y, z) with (R', phi) and a table for corresponding (x, R') with (r, theta). When rotation angle, inter-frame angle, scanning depth for B image or scanning angle are changed, the reconstruction table is reconstructed; otherwise, the reconstruction table is maintained for use. The table look-up module looks up the reconstruction table to obtain R' and phi through y and z coordinates, and then looks up the reconstruction table to obtain r and theta through R' and x coordinate.

The synthesis module transforms a Cartesian coordinate point P(x, y, z) into a polar coordinate point (r, theta, phi), and looks up the gradient table to obtain (p1, p2, p3) through (r, theta, phi), and then calculates the gradient Grad using (p1, p2, p3) as step lengths of three coordinate axes in accordance with the following formula:

$$Grad = (Gr, Gtheta, Gphi)$$
$$= (V(r+\xi \cdot p1, theta, phi) - V(r-\xi \cdot p1, theta, phi),$$
$$V(r, theta+\xi \cdot p2, phi) - V(r, theta-\xi \cdot p2, phi),$$
$$V(r, theta, phi+\xi \cdot p3) - V(r, theta, phi-\xi \cdot p3))$$

where the factor $\xi$ is used to control the step length, which can be selected to be 2.

The ray casting module assigns an initial value 0 to both the gray scale and the opacity. The synthesis module calculates respectively the accumulated gray scale $I_{out}$ and the accumulated opacity $\alpha_{out}$ in accordance with the following formulas:

$$I_{out} = I_{in} + (1-\alpha_{in}) \cdot \alpha_i \cdot C_i \cdot T_i;$$

$$\alpha_{out} = \alpha_{in} + \alpha_i (1-\alpha_{in});$$

Where $I_{in}$ and $I_{out}$ are the accumulated gray scales; $\alpha_{in}$ and $\alpha_{out}$ are the accumulated opacities; $C_i$ and $\alpha_i$ are respectively the gray scale and the opacity of the pixel which the current ray traverses; and $T_i$ is the inner product of unit vector of the gradient and unit vector of the ray direction.

The synthetic condition is a threshold set for the gray scale of the current sampling point. If the gray scale is smaller than the threshold, the sampling point is considered as noise and will not be involved in the synthesis. The threshold is 30 based on different noise levels of different machines.

The termination condition is one of the following conditions:

a) $\alpha_{out} < K$, where $K \leq 1$;
b) the volume data re-sampled with a ray progressing to the last point.

The present invention can avoid a large amount of unnecessary reconstructing calculation by preprocessing and constructing the reconstruction table and the gradient table and transforming the points where calculation is necessary. The present invention would accord with a general situation compared with the prior art, because it is difficult to make the radius for rotating the probe be identical to the radius of the probe.

BRIEF DESCRIPTION OF THE DRAWINGS

FIG. 9 shows an image in two planes, among which
FIG. 9(a) shows the image in a Y-Z plane and FIG. 9(b) shows the image in a R-Z plane that is consistent with a conventional B image.

DETAILED DESCRIPTION OF THE INVENTION

Figure 4:
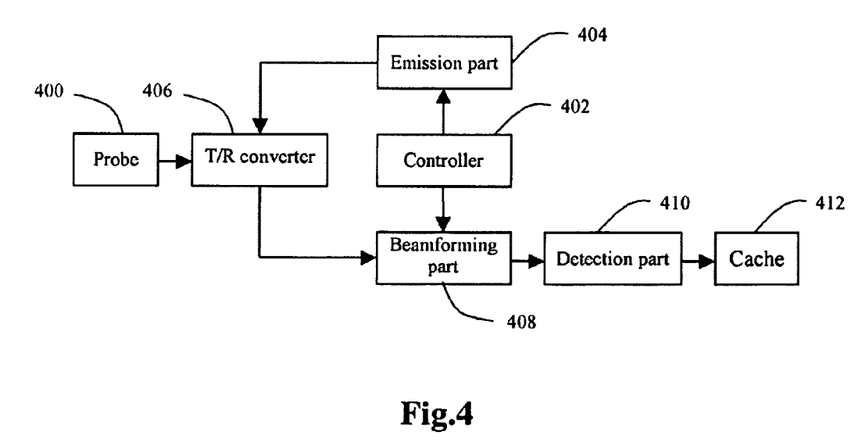
FIG. 4 is a flow chart of data acquisition at the front end of ultrasound imaging according to the embodiments of the present invention.

FIG. 4 is a flow chart of data acquisition at the front end of ultrasound imaging according to the embodiments of the present invention. The probe 400 as used is a mechanical probe that can scan rotatively at a certain velocity driven by a motor. The controller 402 controls an emission part 404 to emit a pulse and controls the probe 400 to rotate at a certain velocity in the mean time. After all array elements emit pulses, the T/R converter 406 switches to the receiving state. Data in all receiving channels are then transmitted to a receiving part 408 where data are subject to beam forming, thus obtaining the scanning line RF data. The RF data are subsequently demodulated by a detection part 410 and re-sampled to obtain data for one scanning line. Scanning line data is stored into a cache 412 as polar coordinates. After the mechanical probe finishes scanning around a specified angle, all desired volume data in polar coordinate form are obtained and then are subject to the subsequent processing.

Figure 5:
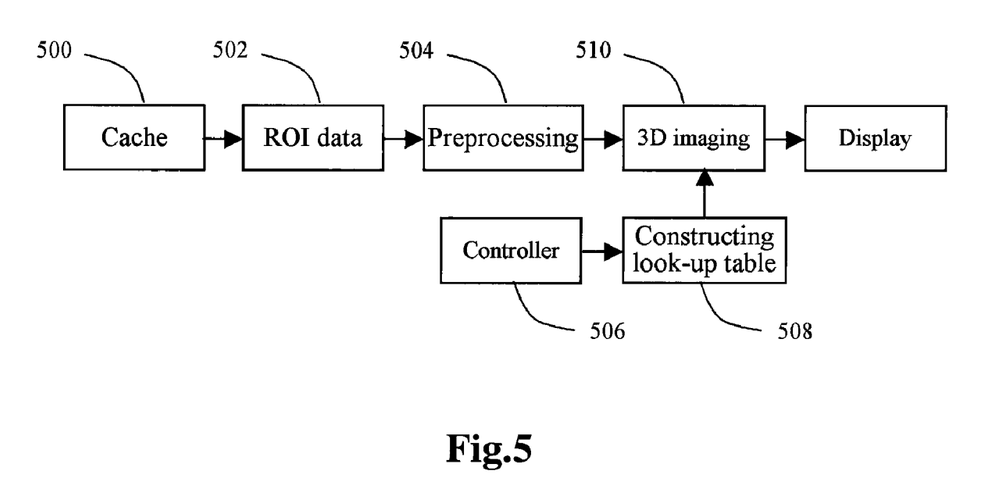
FIG. 5 is a flow chart of data processing according to the embodiments of the present invention.

FIG. 5 is a flow chart of data processing. Not all of the volume data stored in the cache are used for 3D imaging because imaging the regions of interest for 3D ultrasound only can prevent useful data from being covered. Therefore, a user can pick up data concerning regions of interest (ROI) from the cache (block 500) by designating ROI through an interface.

Figure 6:
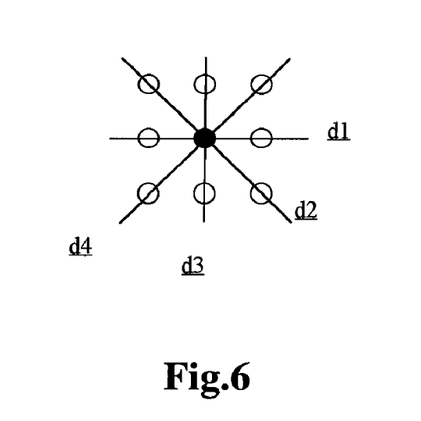
FIG. 6 is a schematic diagram illustrating four directions d1-d4 from the current point.

Due to the ultrasound characteristics, interactions between acoustic waves may cause a lot of speckles in the obtained digital image, which can result in rough edges of an object, such that it is impossible to obtain a smooth and refined image. In order to obtain a better image, the embodiment of the present invention provides a technical solution to preprocess the acquired ROI data (block 502). The object of the preprocessing is to smooth the edges of the image of the object in such a way as to remove speckles and noise. The preprocessing (block 504) may comprise a mean filter, a median filter etc. The embodiment of the present invention employs a direction-based smoothing method. Its basic idea is to select the most uniform direction among various directions from the current point and subject it to the smoothing processing. The advantage of this method is that contrast of the edges is not reduced while smoothing the edges. The most uniform direction for each point may, for example, the one that has the least deviation among the four directions d1-d4 from the current point, as shown in FIG. 6. In principle, variance in each direction is first computed, and the direction has the least variance is considered as the most uniform direction.

Figure 7:
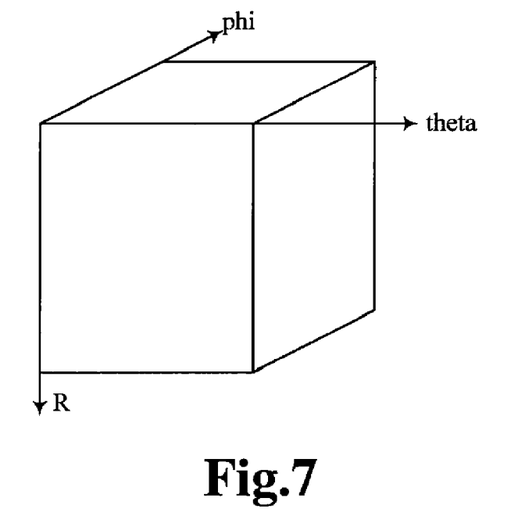
FIG. 7 shows volume data in a polar coordinate system.
Figure 8:
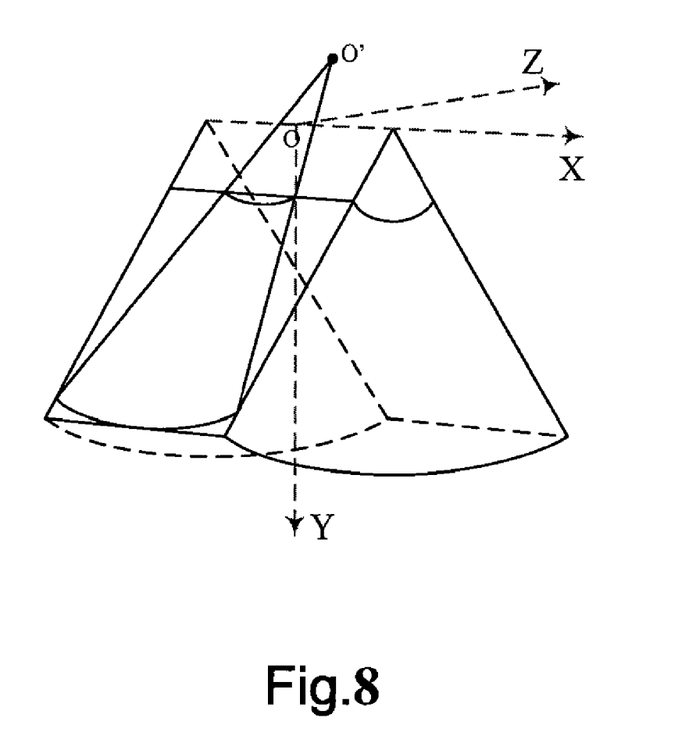
FIG. 8 shows volume data in a Cartesian coordinate system.
Figure 9:
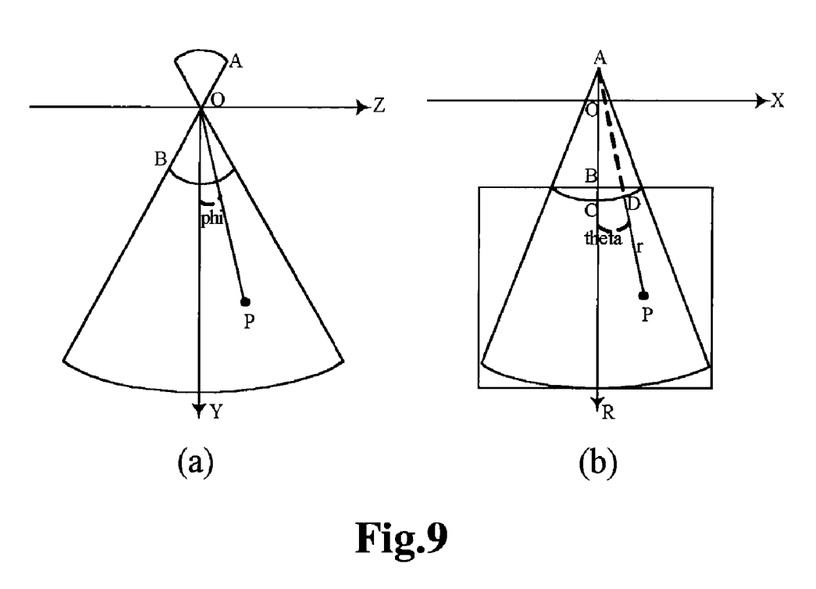

A table look-up module (block 508) controlled by a controller (block 506) is constructed, in which the look-up table includes a reconstruction table and a gradient table. The reconstruction table contains relations for transforming a Cartesian coordinate (x, y, z) to a polar coordinate (r, theta, phi). FIG. 7 shows volume data in a polar coordinate system. R-theta coordinate system describes polar coordinate data in a normal B image, in which R denotes a depth direction; theta denotes angular position of a scanning line; and phi represents the angle the probe rotates around driven by a motor. FIG. 8 shows volume data in a Cartesian coordinate system after reconstruction, in which point O' represents the origin of radius of the probe; O represents the origin of an XYZ coordinate system; and X axis coincides with the direction of a probe support about which the probe rotates. The probe rotates about the OX axis in a plane perpendicular to the YZ plane. FIG. 9 illustrates the transformation between the two polar coordinate systems. P(x, y, z) is a point in the Cartesian coordinate system; fr is the radius of a sector as scanned; and pr is the radius of the probe. FIG. 9(a) is a section of the rotating face of the probe and FIG. 9(b) is a section corresponding to a conventional B image. The following formulas are derivable from FIG. 9(a):

$$R'=|OP|=\sqrt{y^2+z^2},$$

$$\text{phi}=\tan^{-1}(z/y);$$

point P has projection coordinate (x, R') in the XR plane, thus $$r=|AP|-pr=\sqrt{(pr-fr+R')^2+x^2}-pr,$$

$$\text{theta}=\tan^{-1}(x/(pr-fr+R')).$$

It is apparent from the above descriptions how the Cartesian coordinate (x, y, z) is transformed to the polar coordinate (r, theta, phi) using the above-mentioned formulas. A conventional reconstruction method needs the entirety of volume data in the Cartesian coordinate system to be involved in the reconstruction, whereas a very small amount of data is demanded in the ray tracing method. Therefore, it is necessary to store a reconstruction table for maintaining the corresponding relations. The reconstruction table includes a table for corresponding (y, z) with (R', phi) and a table for corresponding (x, R') with (r, theta). In practical application, it is required to perform a discretization on the coordinate R' so that corresponding relations can be established in the two tables. For example, a decimal place of 3 is selected to ensure an accuracy 0.125 for R'. According to the ray tracing method, when it is required to acquire data concerning a certain point in the Cartesian coordinate system, R' and phi are first obtained by looking up y and z coordinates of that point, and then r and theta coordinates by looking up R' and x. Finally, the desired data concerning that point can be obtained by interpolating the corresponding polar coordinate (r, theta, phi) of the volume data.

In addition to the reconstruction table, a gradient table is also constructed. In the subsequent ray tracing algorithm, the gradient at a point is considered in the ray synthesis. Since the gradient at a certain point is computed in the Cartesian coordinate system, a lot of points demand table look-up for multiple times. Assuming that calculation of the gradient at one point involves 6 adjacent points, 6 times of table look-up is required. Moreover, each point should be interpolated using 8 points in the polar coordinate system. Therefore, when computing the gradient at a point, 48 points in the polar coordinate system are required to be involved. Against this background, the embodiment of the present invention calculates an approximate gradient by a table look-up. Using a method reverse to that for deriving the reconstruction, the following can be obtained for a polar coordinate point (r, theta, phi):

x=X(r, theta, phi),
y=Y(r, theta, phi),
z=Z(r, theta, phi).

Derivatives of the coordinates are then calculated, and for each (r, theta, phi), there is $$G = (p1, p2, p3) = \left(\frac{\partial X}{\partial r}, \frac{\partial Y}{\partial theta}, \frac{\partial Z}{\partial phi}\right),$$

which approximates a tensile relation presented when the point concerned is changed from the current position in polar coordinate system to the Cartesian coordinate system. They can be considered to be a direction and a distance in polar coordinate system corresponding to the position (x, y, z) in Cartesian coordinate system. So, a gradient table is constructed, which corresponds to each point in polar coordinate system, in order to store the corresponding (p1, p2, p3). When it is required to calculate the gradient at a point P(x, y, z) in Cartesian coordinate system, the coordinates of point P are transformed into polar coordinates (r, theta, phi). (p1, p2, p3) are obtained by looking up the gradient table through (r, theta, phi) and then used as step lengths of the three coordinate axes to calculate the gradient. Assuming the volume data in polar coordinate to be V, the gradient Grad can be calculated as follows:

$$\begin{aligned}Grad &= (Gr, Gtheta, Gphi) \\ &= (V(r+\xi \cdot p1, theta, phi) - V(r-\xi \cdot p1, theta, phi), \\ &\quad V(r, theta+\xi \cdot p2, phi) - V(r, theta-\xi \cdot p2, phi), \\ &\quad V(r, theta, phi+\xi \cdot p3) - V(r, theta, phi-\xi \cdot p3))\end{aligned}$$

where a factor $\xi$ is used to control the step length, which can be selected to be 2.

It is not necessary to reconstruct the reconstruction table for each and every newly scanned volume data. The reconstruction table can remain unchanged so long as the factors which constitute the reconstruction table remain unchanged, such as the rotation angle, the inter-frame angle, the scanning depth for B image or scanning angle etc. When changes happen to these factors, the controller will control a table constructing module to reconstruct a table based on new factors. In fact, parameters for the new reconstructed environment do not change significantly, so the existing reconstructed table may be used to accelerate the construction of a new table. For example, if changes happen to the rotation angle only, the existing reconstruction table and the existing gradient table can be maintained so long as the excessive reconstructed portion is calculated (in the case where the rotation angle becomes larger) or the excessive transformed portion is deleted (in the case where the rotation angle becomes smaller). That is to say, table reconstruction for a new angle may be accelerated by the existing reconstructed table for a certain angle. For example, if the old angle is 50 degree and the new angle is 40 degree, it is possible to directly interpolate the old reconstruction table to obtain a new one. If changes happen to the inter-frame angle, it is necessary to reconstruct a new table. In this case, the desired new reconstruction table can be obtained by interpolation based on the existing table, whereby calculations, such as trigonometric function transformation are not necessary.

Figure 10:
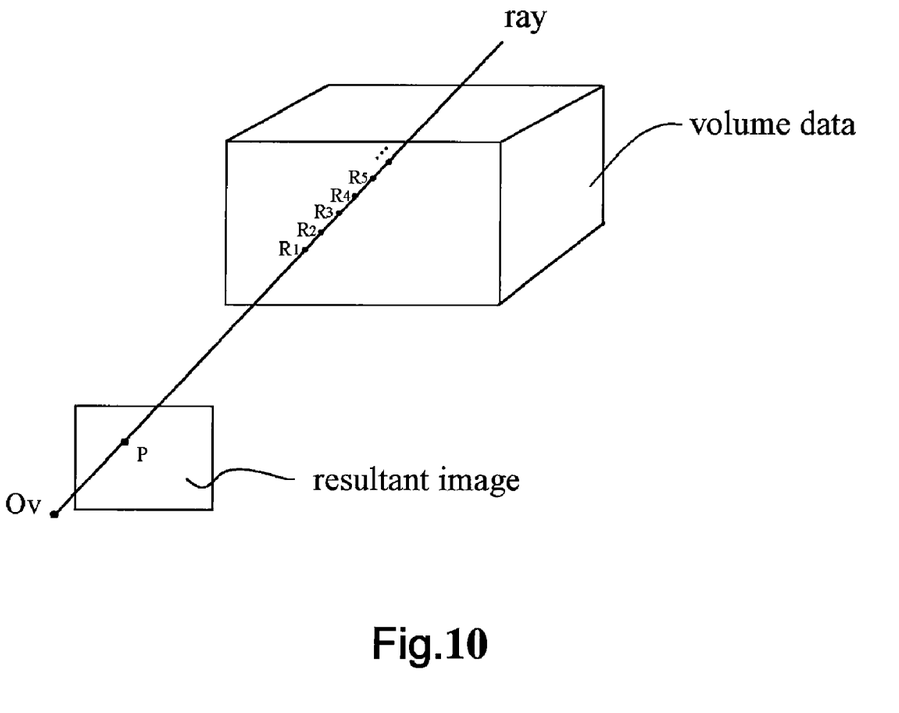
FIG. 10 illustrates volume data re-sampling using the ray traversing the resultant image and viewpoint Ov.

The 3D imaging (block 510) uses a ray tracing method. As shown in FIG. 10, Ov is the viewpoint, and P is a point in the resultant image. In order to calculate values concerning point P, the line connecting the viewpoint to point P is considered as the ray direction. The ray passes through the volume data which are sampled to obtain points R1~RN. Data concerning point P can be obtained by performing a ray synthesis on these points R1~RN.

For each of the volume data, there may be an opacity α that is a monotone linear function proportional to the gray scale.

Figure 11:
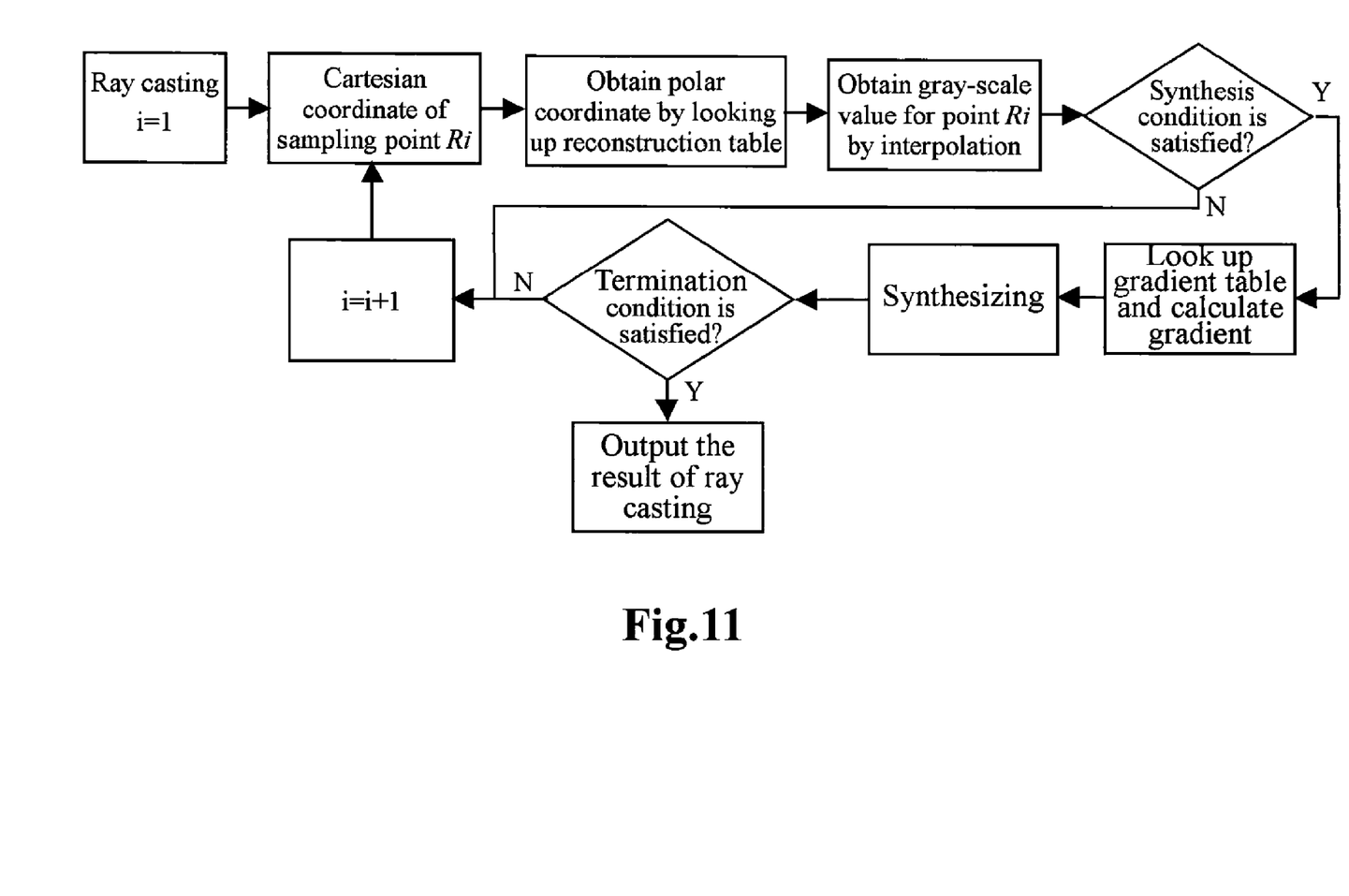
FIG. 11 is a flow chart of a ray casting process according to the embodiments of the present invention.
Figure 12:
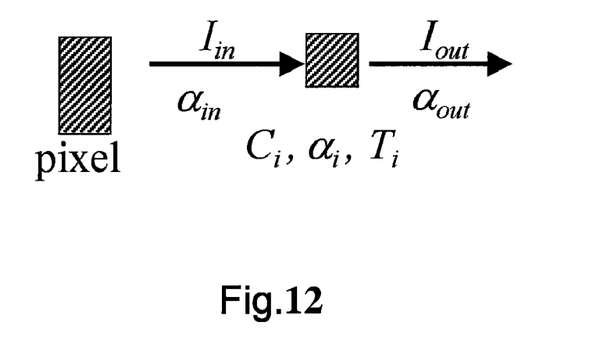
FIG. 12 illustrates a ray synthesizing method according to the embodiments of the present invention, in which $I_{in}$ and $I_{out}$ are accumulation values; $\alpha_{in}$ and $\alpha_{out}$ are accumulated opacity values; $C_i$ and $\alpha_i$ respectively represent a gray scale and an opacity value of the pixel through which the current ray passes; and Ti represents the inner product of unit vector of the gradient and unit vector of the ray direction.

As shown in FIG. 11 and FIG. 12, the ray casting process comprises the follows:

1) assigning initial values $I_{in}=0$, $\alpha_{in}=0$, i=1;
2) looking up the table to obtain a polar coordinate for a sampling point Ri through its Cartesian coordinate;
3) calculating a gray-scale value Ci for point Ri by interpolation;
4) looking up the gradient table and calculating a gradient Grad for this point;
5) calculating the inner product Ti of unit vector of the gradient and unit vector of the ray direction;
6) calculating an accumulated gray scale $I_{out}$ and $\alpha_{out}$:

$$I_{out}=I_{in}+(1-\alpha_{in})\cdot\alpha_i\cdot C_i\cdot T_i,$$

$$\alpha_{out}=\alpha_{in}+\alpha_i\cdot(1-\alpha_{in});$$

7) $I_{in}=I_{out}$, $\alpha_{in}=\alpha_{out}$;
8) outputting the current $I_{out}$ as a value corresponding to the pixel of the resultant image, if the termination condition is satisfied; otherwise, i=i+1 and skipping to 2).

The synthesis condition as referred to in FIG. 11 means a threshold set for the gray scale of the current sampling point. If the gray scale is smaller than the threshold, the point is considered as noise, and the synthesis step will not involve that point. The threshold is generally set as 30 in accordance with different noise levels of different machines.

The termination condition is generally one of the follows:
a) $\alpha_{out}<K$, K representing an accumulated opacity value. In fact, when the accumulated opacity value reaches 1, the subsequent re-sampled points will be covered entirely by the preceding points. Moreover, selecting the condition K<1 is to ensure that the obtained gray scale is synthesized by the values on the surface only, so that the points inside the tissue will not be displayed, and the time for terminating ray casting will be reduced;
b) the volume data re-sampled with a ray progressing to the last point.

For each pixel on the resultant image, the gray scale of ray synthesis is calculated by emitting rays to finally form the image.

Figure 13:
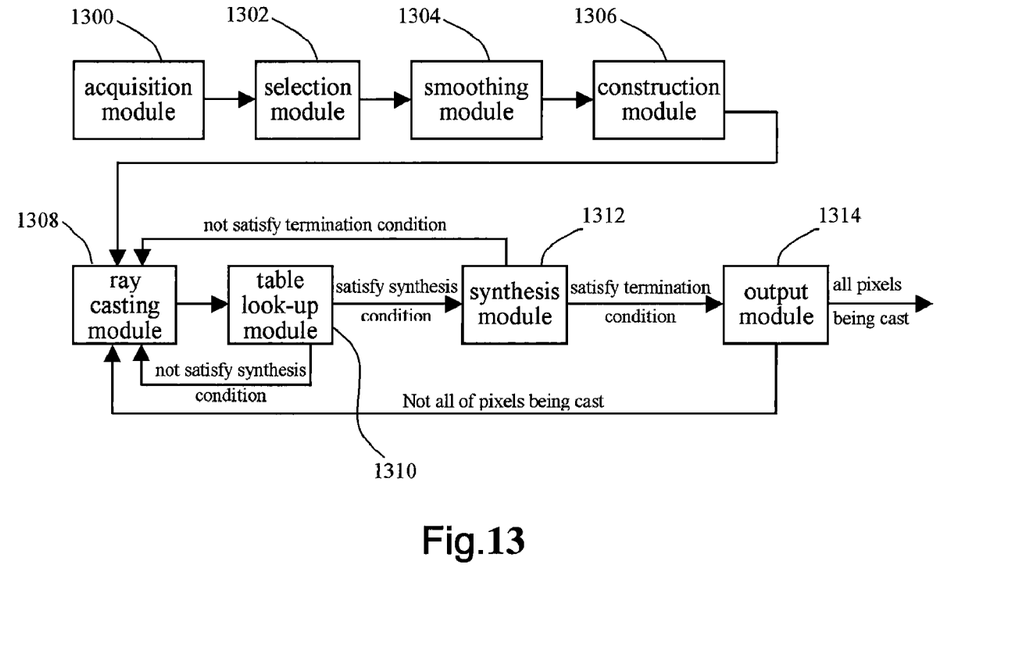
FIG. 13 is a block diagram of an apparatus for fast 3D ultrasound imaging according to the embodiments of the present invention.

FIG. 13 is a block diagram of an apparatus for fast 3D ultrasound imaging according to the embodiment of the present invention. The apparatus comprises an acquisition module 1300, a selection module 1302, a smoothing module 1304, a construction module 1306, a ray casting module 1308, a table look-up module 1310, a synthesis module 1312 and an output module 1314. The acquisition module 1300 scans and acquires volume data in polar form, which are then stored in a cache. The selection module 1302 is optional, whereby the user may set a region of interest via an interface and select data concerning the region of interest from the cache and transmit the selected data to the smoothing module 1304 and the subsequent modules for processing. The smoothing module 1304, which is optional also, smoothes the acquired volume data. The construction module 1306 constructs a reconstruction table and a gradient table, among which the reconstruction table contains relations for transforming a Cartesian coordinate into a polar coordinate, and the gradient table contains (p1,p2,p3) corresponding to a polar coordinate point (r, theta, phi), where $$G=(p1,p2,p3)=\left(\frac{\partial X}{\partial r},\frac{\partial Y}{\partial theta},\frac{\partial Z}{\partial phi}\right).$$

The ray casting module 1308 selects an initial sampling point, assigns initial values to the gray scale and opacity of the point and obtains a Cartesian coordinate of the sampling point by casting. The table look-up module 1310 obtains a polar coordinate by looking up the table through the Cartesian coordinate of the sampling point and calculates gray scale of the sampling point by interpolation. If the gray scale at a sampling point as calculated meets a synthesis condition, that sample point will be synthesized in the synthesis module 1312, while those that do not meet the synthesis condition will be returned back to the ray casting module 1308 to be re-sampled. If the gray scale value meets the synthesis condition, the gradient of that sampling point will be calculated by the synthesis module 1312 by looking up the gradient table. The synthesis module 1312 then calculates inner product of unit vector of the gradient and unit vector of the ray direction, and subsequently calculates an accumulated gray scale and an accumulated opacity based on the inner product. The output module 1314 outputs the currently accumulated gray scale value as a result for corresponding pixel of a resultant image if a predetermined termination condition is satisfied. Otherwise the process will return back to the ray casting module 1308. Where the termination condition is met, it is only a certain ray that is to be terminated, and only one pixel of the resultant image is output. Therefore, only upon a plurality of ray castings can one frame of 3D image be formed and output. As shown in FIG. 13, many modules communicate to the ray casting module. First, the ray casting module 1308 will be effected after data construction. Second, when the synthesis condition or the termination condition is not satisfied, the ray casting module 1308 will start functioning in order to pick up the next sampling point. Finally, after the output module 1314 outputs the gray scale value of the pixel synthesized by the casting ray, if there are no pixels to be cast, the ray casting module 1308 will still be effected to start ray casting and sampling of the next pixel.

Figure 14:
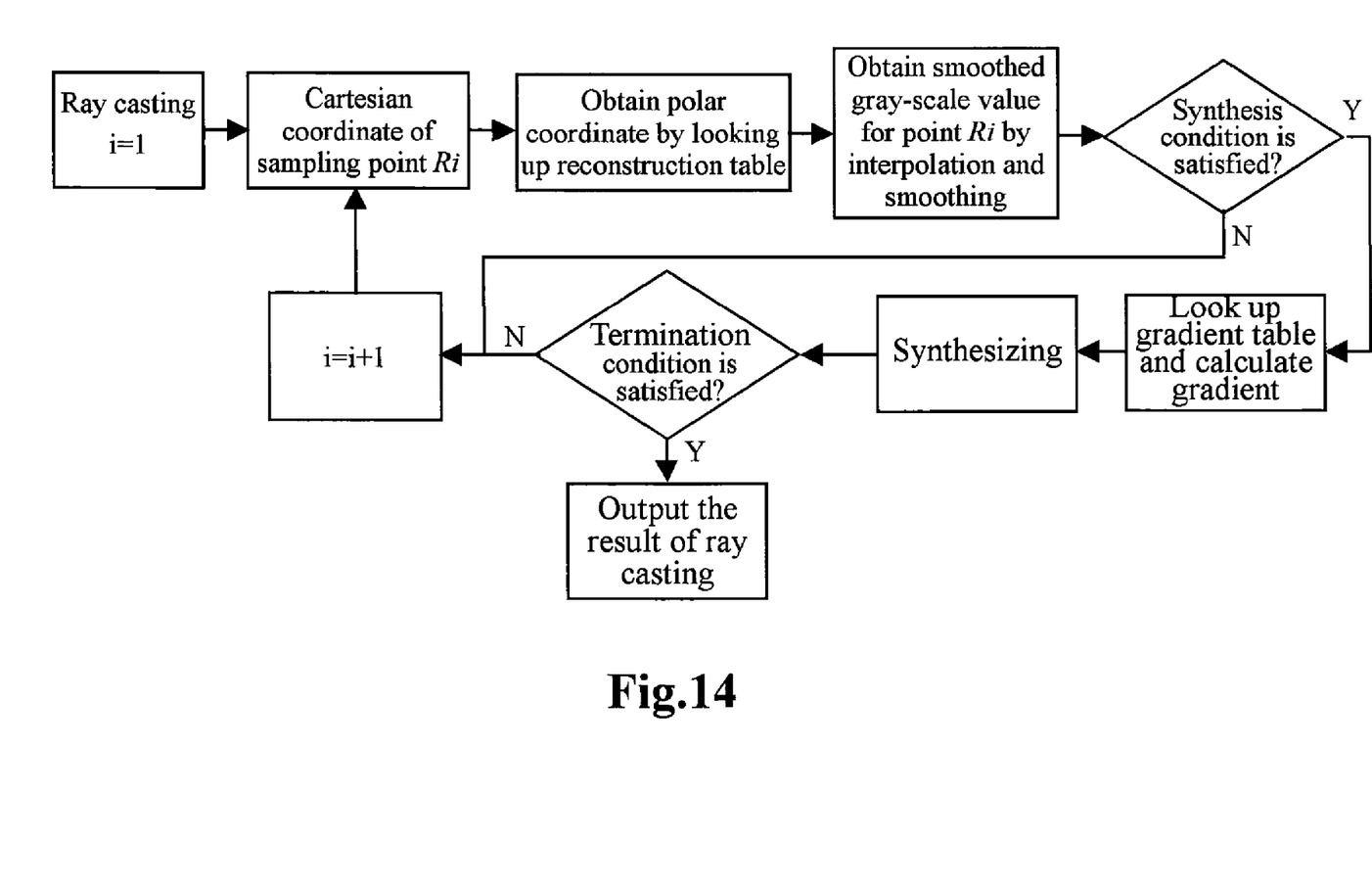
FIG. 14 is a flow chart of another ray casting process according to the embodiments of the present invention.
Figure 15:
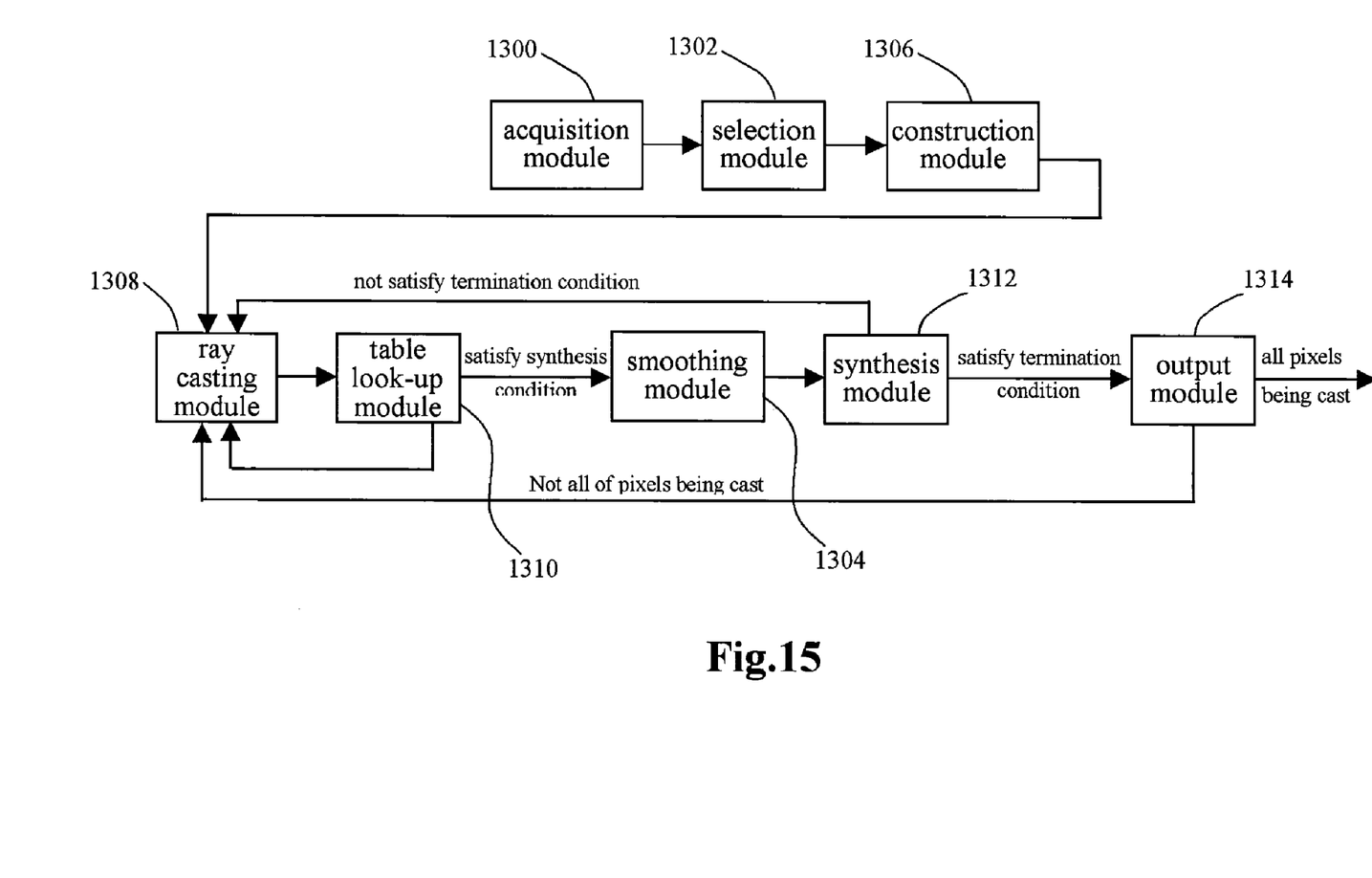
FIG. 15 is a block diagram of another apparatus for fast 3D ultrasound imaging according to the embodiments of the present invention.

According to the embodiment of the present invention, the smoothing step may also be performed after the ray synthesis. That is, only when the sampling points are desired will the result for the smoothing step be calculated in real time. In this way, the amount of calculation is reduced, and an accurate approximation is reachable. FIG. 14 shows a flow chart of ray casting, in which the smoothing is implemented after the ray synthesis, and other steps are the same as those described hereinbefore. FIG. 15 is a block diagram of an apparatus for fast 3D ultrasound imaging, in which the smoothing is implemented after the ray synthesis, and other structures are the same as those described hereinbefore.

The present invention has been described in details by way of above-mentioned specific embodiments, but the present invention is not limited to these specific embodiments. A person skilled in the art may understand that many modifications, alternations, equivalent substitutions can be made without departing from the spirit of the present invention, and should be considered as within the protective scope of the present invention defined by the attached claims.

The invention claimed is:

1. A method for 3D ultrasound imaging, comprising steps of:

acquiring volume data associated with polar coordinate locations (r, theta, phi) from a scanning operation of a mechanical ultrasound probe;

storing the volume data in a cache;

constructing a reconstruction table and a gradient table, wherein the reconstruction table contains entries associating the polar coordinate locations of the volume data with equivalent Cartesian coordinate locations (X, Y, Z), and the gradient table contains entries (p1, p2, p3) for each polar coordinate location of the reconstruction table calculated according to:

$$(p1, p2, p3) = \left(\frac{\partial X}{\partial r}, \frac{\partial Y}{\partial theta}, \frac{\partial Z}{\partial phi}\right);$$

casting rays to determine an initial sampling point which is assigned with an initial gray scale and an initial opacity;

obtaining a Cartesian coordinate location of the initial sampling point;

obtaining a polar coordinate location of the initial sampling point according to the initial sampling point's Cartesian coordinate location using the reconstruction table and interpolating gray scale values of locations surrounding the initial sample point to derive an actual gray scale value of the initial sampling point;

in response to determining that the actual gray scale value meets a synthetic condition, calculating a gradient of the initial sampling point using the gradient table, and calculating an inner product of a unit vector of the gradient, a unit vector of a ray direction of the initial sampling point, and an accumulated gray scale and an accumulated opacity based in part on the initial gray scale and the initial opacity; and in response to determining that a predetermined termination condition is satisfied, outputting the accumulated gray scale for the pixel corresponding to the initial sampling point on a 3D resultant image.

2. The method according to claim 1, further comprising step of:

smoothing the volume data.

3. The method according to claim 2, wherein the smoothing step is executed after the obtaining a polar coordinate location of the initial sampling point step, so as to smooth the volume data at the initial sampling point and obtain the smoothed data of the volume data at the polar coordinate location of the initial sampling point.

4. The method according to claim 1, further comprising step of:

designating a region of interest via an interface; and selecting data concerning the region of interest from the cache.

5. The method according to claim 1, further comprising performing smoothing processing using a mean filter or a median filter.

6. The method according to claim 1, wherein the method is carried out along a uniform direction among various directions of the initial sampling point.

7. The method according to claim 1, wherein when a rotation angle, an inter-frame angle, a scanning depth for a B image or a scanning angle of the mechanical ultrasound probe are changed, the reconstruction table is reconstructed.

8. The method according to claim 1, further comprising calculating a gradient of the initial sampling point using the gradient table comprising:

transforming a Cartesian coordinate point location ($x_1$, $y_1$, $z_1$) into a polar coordinate point location ($r_1$, $theta_1$, $phi_1$);

obtaining entries (p1, p2, p3) for the polar coordinate point location (r, theta, phi) using the gradient table; and calculating a gradient Grad using the entries (p1, p2, p3) as step lengths of three coordinate axes according to:

$$Grad = (Gr, Gtheta, Gphi)$$
$$= (V(r + \xi \cdot p1, theta, phi) - V(r - \xi \cdot p1, theta, phi),$$
$$V(r, theta + \xi \cdot p2, phi) - V(r, theta - \xi \cdot p2, phi),$$
$$V(r, theta, phi + \xi \cdot p3) - V(r, theta, phi - \xi \cdot p3))$$

where the factor $\xi$ is used to control the step length.

9. The method according to claim 1, wherein the initial gray scale and the initial opacity are both 0.

10. The method according to claim 1, wherein the accumulated gray scale $I_{out}$ and the accumulated opacity $\alpha_{out}$ are calculated according to:

$$I_{out} = I_{in} + (1 + \alpha_{in}) \cdot \alpha_i \cdot C_i \cdot T_i;$$

$$\alpha_{out} = \alpha_{in} + \alpha_i \cdot (1 - \alpha_{in});$$

where $I_{in}$ is the accumulated gray scale input and $I_{out}$ is the accumulated scale output; $\alpha_{in}$ is the accumulated gray scale opacity input and $\alpha_{out}$ is the accumulated gray scale opacity output; $C_i$ and $\alpha_i$ are a gray scale and the opacity of a pixel which the cast ray traverses respectively; and $T_i$ is the inner product of an unit vector of the gradient and an unit vector of the ray direction.

11. The method according to claim 1, wherein the synthetic condition is a threshold for the actual gray scale, and wherein if the actual gray scale is smaller than the threshold, the initial sampling point concerned is considered as noise, the threshold being based on a noise level of an ultrasound imaging machine.

12. An apparatus for 3D ultrasound imaging, comprising:

an acquisition module for acquiring volume data associated with polar coordinate locations (r, theta, phi) from a scanning operation of a mechanical ultrasound probe;

a construction module for constructing a reconstruction table and a gradient table, wherein the reconstruction table contains entries associate the polar coordinate locations of the volume data with equivalent Cartesian coordinate locations (X, Y, Z), and the gradient table contains entries for each polar coordinate location of the reconstruction table calculated according to:

$$(p1, p2, p3) = \left(\frac{\partial X}{\partial r}, \frac{\partial Y}{\partial theta}, \frac{\partial Z}{\partial phi}\right);$$

a ray casting module for casting rays to determine an initial sampling point which is assigned with an initial gray scale value and an initial opacity value, and to obtain a Cartesian coordinate location of the initial sampling point;

a table look-up module for using the reconstruction table to obtain a polar coordinate location of the initial sampling point according to the initial sampling point's Cartesian coordinate location, wherein the gray scale values of locations surrounding the initial sample point are subjected to interpolation to derive an actual gray scale value of the initial sampling point;

a synthesis module for calculating a gradient of the initial sampling point using the gradient table based on a determination that the actual gray scale value meets a synthetic condition, for calculating an inner product of a unit vector of the gradient, a unit vector of a ray direction, an accumulated gray scale, and an accumulated opacity based in part on the initial gray scale value and the initial opacity; and an output module for outputting the current accumulated gray scale for the pixel corresponding to the initial sampling point on a 3D resultant image in response to determining that if a predetermined termination condition is satisfied.

13. The apparatus according to claim 12, further comprising:
a smoothing module for smoothing the volume data.

14. The apparatus according to claim 12, further comprising:
a selection module for designating a region of interest via an interface and for selecting data concerning the region of interest from the cache.

15. The apparatus according to claim 13, wherein the smoothing module performs a mean filter or a median on the volume data.

16. The apparatus according to claim 13, wherein the smoothing module carries out the smoothing along a uniform direction among various directions of the initial sampling point.

17. The apparatus according to claim 12, wherein when a rotation angle, a frame-to-frame angle, a scanning depth for a B image or a scanning angle of the mechanical ultrasound probe are changed, the reconstruction table is reconstructed.

18. The apparatus according to claim 12, wherein the synthesis module transforms a Cartesian coordinate point location $(x_1, y_1, z_1)$ into a polar coordinate point location $(r_1, theta_1, phi_1)$ obtains entries (p1, p2, p3) for the polar coordinate point location (r, theta, phi) using the gradient table, and calculates a gradient Grad using (p1, p2, p3) as step lengths of three coordinate axes in according to:

$$Grad = (Gr, Gtheta, Gphi)$$
$$= (V(r + \xi \cdot p1, theta, phi) - V(r - \xi \cdot p1, theta, phi),$$
$$V(r, theta + \xi \cdot p2, phi) - V(r, theta - \xi \cdot p2, phi),$$
$$V(r, theta, phi + \xi \cdot p3) - V(r, theta, phi - \xi \cdot p3))$$

$$I_{out} = I_{in} + (1 - \alpha_{in}) \cdot \alpha_i \cdot C_i \cdot T_i;$$

$$\alpha_{out} = \alpha_{in} + \alpha_i \cdot (1 - \alpha_{in});$$

where the factor is used to control the step length.

19. The apparatus according to claim 12, wherein the ray casting module assigns an initial value 0 to both the gray scale and the opacity.

20. The apparatus according to claim 12, wherein the synthesis module calculates the accumulated gray scale $I_{out}$ and the accumulated opacity $\alpha_{out}$ according to:

$$I_{out} = I_{in} + (1 + \alpha_{in}) \cdot \alpha_i \cdot C_i \cdot T_i;$$

$$\alpha_{out} = \alpha_{in} + \alpha_i \cdot (1 - \alpha_{in});$$

where $I_{in}$ is the accumulated gray scale input and $I_{out}$ is the accumulated scale output; $\alpha_{in}$ is the accumulated gray scale opacity input and $\alpha_{out}$ is the accumulated gray scale opacity output; $C_i$ and $\alpha_i$ are a gray scale and the opacity of the pixel which the cast ray traverses respectively; and $T_i$ is the inner product of an unit vector of the gradient unit and an unit vector of the ray direction.

* * * * *